(12) United States Patent
Umezu et al.

(10) Patent No.: US 8,043,854 B2
(45) Date of Patent: Oct. 25, 2011

(54) METHOD OF DECELLULARIZING TISSUES

(75) Inventors: Mitsuo Umezu, Tokyo (JP); Kiyotaka Iwasaki, Tokyo (JP); Shigeyuki Ozaki, Tokyo (JP); Yuji Morimoto, Tokyo (JP); Osamu Endo, Tokyo (JP)

(73) Assignees: Waseda University, Tokyo (JP); Selfusion Inc., Tokyo (JP)

( * ) Notice: Subject to any disclaimer, the term of this patent is extended or adjusted under 35 U.S.C. 154(b) by 1749 days.

(21) Appl. No.: 10/556,400

(22) PCT Filed: May 12, 2004

(86) PCT No.: PCT/JP2004/006662
§ 371 (c)(1),
(2), (4) Date: Nov. 10, 2005

(87) PCT Pub. No.: WO2004/100831
PCT Pub. Date: Nov. 25, 2004

(65) Prior Publication Data
US 2006/0212074 A1 Sep. 21, 2006

(30) Foreign Application Priority Data
May 15, 2003 (JP) ................................. 2003-138015

(51) Int. Cl.
*A01N 1/00* (2006.01)
(52) U.S. Cl. .......... 435/378; 435/1.1; 435/1.2; 623/901; 607/101
(58) Field of Classification Search ........................ None
See application file for complete search history.

(56) References Cited

U.S. PATENT DOCUMENTS

| 4,250,139 | A  | * | 2/1981 | Luck et al. ....................... 422/21 |
| 2004/0052830 | A1 | * | 3/2004 | Konertz et al. ............... 424/423 |
| 2006/0115900 | A1 | * | 6/2006 | Fujisato et al. ............... 435/378 |

FOREIGN PATENT DOCUMENTS

| JP | 4-288165 A | 10/1992 |
| JP | 6-261933 | 9/1994 |
| JP | 2002-536109 | 10/2002 |
| JP | 2004-187952 | 7/2004 |
| WO | WO 00/47131 | 8/2000 |

OTHER PUBLICATIONS

Kiyotaka Iwasaki et al.; "Development of two types of novel bioreactors for decellularization and in vitro pulsatile conditioning of endothelial cells cultured on the porcine aortic valves", The Japan Society of Mechanical Engineers, Mar. 13, 2003, pp. 83-84.
C. E. Visser et al.; "Microwave treatment of xenogeneic cartilage transplants", Biomaterials, vol. 10, 1989, pp. 507-510.

* cited by examiner

*Primary Examiner* — Allison Ford
(74) *Attorney, Agent, or Firm* — Westerman, Hattori, Daniels & Adrian, LLP

(57) ABSTRACT

In the transplant of a living organism tissue, such as a heart valve, taken from an animal, etc. into a human body, a cell removing solution for removing original cells from the living organism tissue is provided with flow approximately equal to the bloodstream of transplant recipient living body, and the living organism tissue is placed in the flow so as to effect immersion of the living organism tissue in the cell removing solution. In the immersion, it is preferred that the living organism tissue placed in the cell removing solution, while being rotated, be irradiated with microwave. As a result, original cells can be removed from the living organism tissue uniformly and reliably, so that the biocompatibility of living organism tissue after transplant can be enhanced.

2 Claims, 12 Drawing Sheets (A)

| | CONDITIONS | REMAINING NUMBER PER UNIT AREA (number/mm²) |
|---|---|---|
| EXAMPLE1 | 100W 8 HOURS | 850 |
| EXAMPLE2 | 500W 12 HOURS | 380 |
| | 500W 24 HOURS | 0 |
| | | 0 |
| | | 970 |
| COMPARATIVE EXAMPLE1 | NO PROCESSING | 1880 |

METHOD OF DECELLULARIZING TISSUES

TECHNICAL FIELD

This invention relates to a cell-removing method, and more particularly, to a cell-removing method enhanced in cell removing effect from a living organism tissue in transplanting a living organism tissue.

BACKGROUND ART

When a heart valve of a human body does not normally work, causing embarrassments as constriction of the opening of the heart valve and reflux of blood, the heart valve must be replaced by a substitute valve. As the substitute valve presently used, mention may be made of a mechanical valve formed of a artificial material, a xenogenic bioprosthetic valve taken from an animal such as a pig, and an allogeneic bioprosthetic valve donated from another human body, etc. These valves have the following problems. Although the mechanical valve is durable, the recipient must take an anticoagulant for the entire lifetime. On the other hand, in the xenogenic bioprosthetic valve, the recipient needs not to take an anticoagulant for the lifetime; however deposition of calcium and the like takes place for a long time, causing malfunction in the valve, with the result that the valve must be exchanged with a new substitute valve at an interval of about 15 years. Furthermore, in the case of the allogeneic bioprosthetic valve, because the number of donors is limited, a sufficiently large number of allogeneic bioprosthetic valves are not easily obtained.

Of them, the xenogenic bioprosthetic valve is prospective for the reasons that a sufficient number of valves can be provided and patients are not necessary to take an anticoagulant for their lifetime after transplant. Therefore, the xenogenic bioprosthetic valve is expected to be more useful than other substitute valves only if the drawback of poor durability is overcome.

In the context, the following method is known which suppresses the post-transplant immunological rejection and improves the durability of a xenogenic bioprosthetic valve taken from an animal such as a pig (for example, see Japanese Publication No. 6-261933). In this method, a xenogenic bioprosthetic valve is first immersed in a cell-removing solution such as bile acid or a surfactant, thereby removing cells originated from the animal such as endothelial cells and fibroblast cells (cell-removing process). Then, the xenogenic bioprosthetic valve from which original cells have been removed is immersed in a cell-containing solution containing autologous cells, such as endothelial cells and fibroblast cells, taken from a recipient human body (to which the xenogenic bioprosthetic valve is to be transplanted), thereby seeding the autologous cells in the xenogenic bioprosthetic valve (cell-seeding process).

However, in the processing method mentioned above, since a xenogenic bioprosthetic valve taken from an animal cannot be efficiently treated in the cell-removing process and cell-seeding process, the resultant xenogenic bioprosthetic valve fails to acquire sufficient biocompatibility. In other words, since original cells more or less remain in the cell-removing process, the biocompatibility of the resultant xenogenic bioprosthetic valve decreases due to the presence of the original cells.

In these circumstances, the this inventors have intensively conducted experimental studies with the view toward overcoming the aforementioned problems. They devised a method of supplying the cell-removing solution for immersing a xenogenic bioprosthetic valve at a flow rate virtually corresponding to the human blood flow and/or irradiating the xenogenic bioprosthetic valve immersed in the cell-removing solution with microwave. As a result, they found that the number of remaining original cells significantly decreases by this method.

DISCLOSURE OF THE INVENTION

This invention was conceived based on such a finding. An object of the invention is to provide a method of efficiently removing original cells present in the living organism tissue such as a xenogenic bioprosthetic valve, thereby enhancing the biocompatibility of the living organism tissue after transplant.

To attain the object, the present invention is directed to a cell-removing method for removing original cells from a predetermined living organism tissue when the living organism tissue is transplanted, comprising immersing the living organism tissue in a predetermined cell-removing solution, in which the cell-removing solution is allowed to flow in a state of a pulsatile flow by applying a predetermined pulse to the cell-removing solution and the living organism tissue is placed in the pulsatile flow. By virtue of this method, the number of remaining original cells in the living organism tissue can be significantly reduced compared to conventional methods, thereby enhancing the biocompatibility of the living organism tissue after transplant.

Furthermore, the present invention is directed to a cell-removing method for removing original cells from a predetermined living organism tissue when the living organism tissue is transplanted, comprising immersing the living organism tissue in a cell-removing solution, in which the living organism tissue placed in the cell-removing solution is irradiated with microwave. The aforementioned object can be attained also by this method.

The (latter) method may be preferably performed simultaneously with the method in which the cell-removing solution is allowed to flow in a state of pulsatile flow by applying a predetermined pulse to the cell-removing solution and the living organism tissue is placed in the pulsatile flow. By virtue of this approach, the effect of removing cells can be further enhanced and the original cells can be almost completely eliminated from the living organism tissue.

Microwave is applied while rotating the living organism tissue relative to a microwave irradiation site. In this manner, microwave can be applied to the living organism tissue virtually uniformly along the rotation circumference direction, with the result that cells can be removed virtually uniformly from almost the entire region of the living organism tissue along the rotation circumference direction.

BRIEF DESCRIPTION OF THE DRAWINGS

FIG. 11 is a Table showing the number of remaining original cells per unit area in Example 1, 2 in comparison with Comparative Example 1;

BEST MODE FOR CARRYING OUT THE INVENTION

Now, an embodiment of the present invention will be described with reference to the accompanying drawings.

Figure 1:
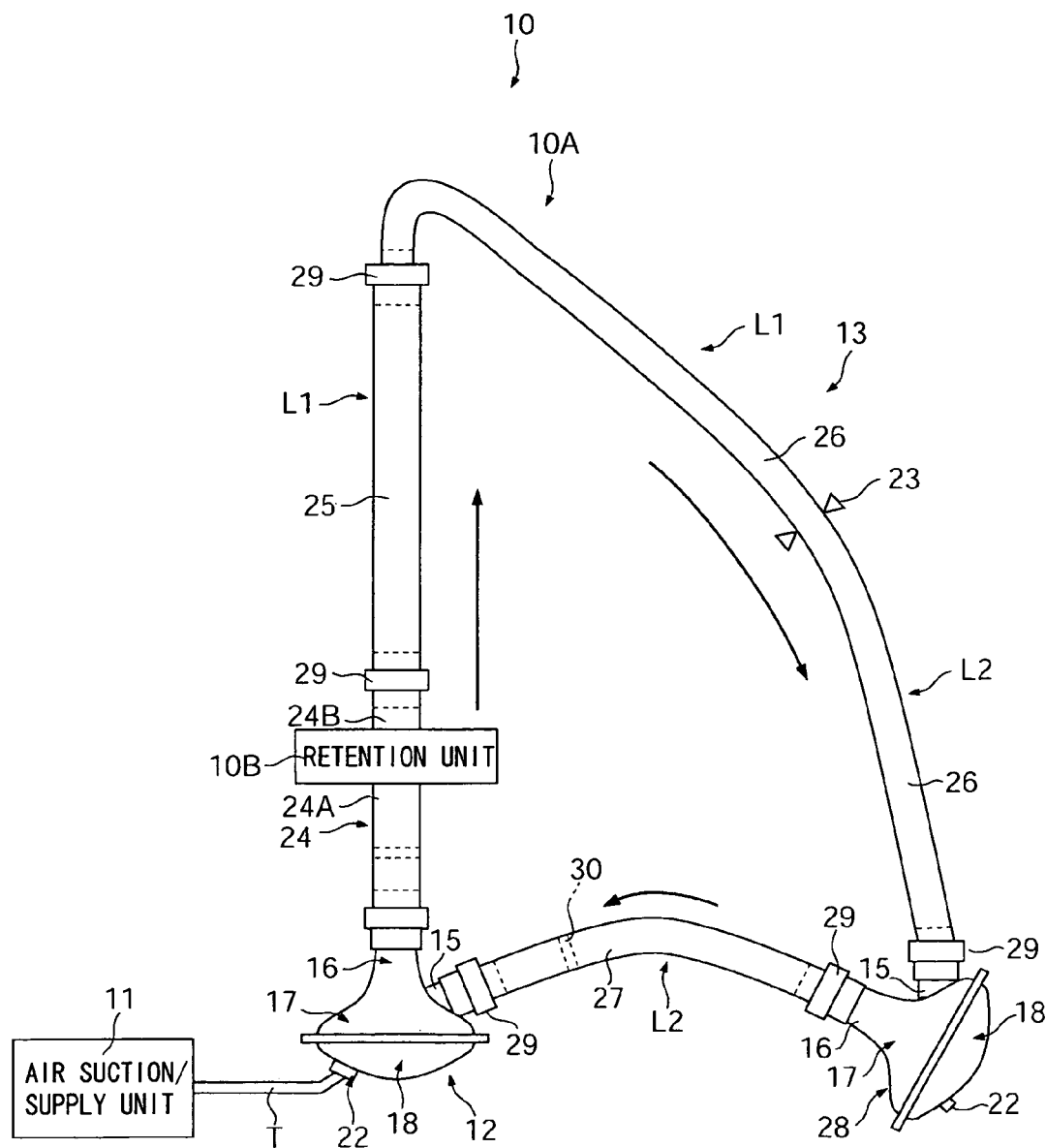
FIG. 1 is a view showing the schematic structure of the living organism tissue processing apparatus to be applied to this invention.

FIG. 1 is a view showing the schematic structure of a living organism tissue processing apparatus according to this invention. The living organism tissue processing apparatus 10 shown in the figure is used in a cell-removing process and a cell-seeding process of a living organism tissue of a xenogenic bioprosthetic valve. The cell-removing process is performed before a xenogenic bioprosthetic valve, which is taken from an animal such as a pig, is transplanted to a human body. The cell-removing process is performed by immersing the xenogenic bioprosthetic valve in a cell-removing solution such as bile acid, thereby removing the animal cells (hereinafter referred to as "original cells") to obtain only a substrate formed of collagen, etc. On the other hand, the cell-seeding process is performed by immersing the xenogenic bioprosthetic valve from which the original cells have been removed in a cell-containing solution containing the cells (hereinafter referred to as "autologous cells") of a recipient's human body (to which the xenogenic bioprosthetic valve is to be transplanted), thereby adhering the autologous cells to the substrate.

The living organism tissue processing apparatus 10 comprises a circulation apparatus 10A for circulating the cell-removing solution and the cell-containing solution through a predetermined circuit, and a retention unit 10B attached to the circulation apparatus 10A for retaining a xenogenic bioprosthetic valve. Note that, if not otherwise specified, the cell-removing solution and the cell-containing solution are collectively referred to as "the solution".

The circulation apparatus 10A comprises a known air suction/supply unit 11, a driving pump 12 formed of polyurethane and connected to the air suction/supply unit 11, and a circulation channel 13 arranged such that the solution discharged from the driving pump 12 returns to the driving pump 12.

The air suction/supply unit 11 has a known structure capable of suctioning air out from the driving pump 12 and supplying air into the driving pump 12. The detail description of the structure is omitted herein.

Figure 2:
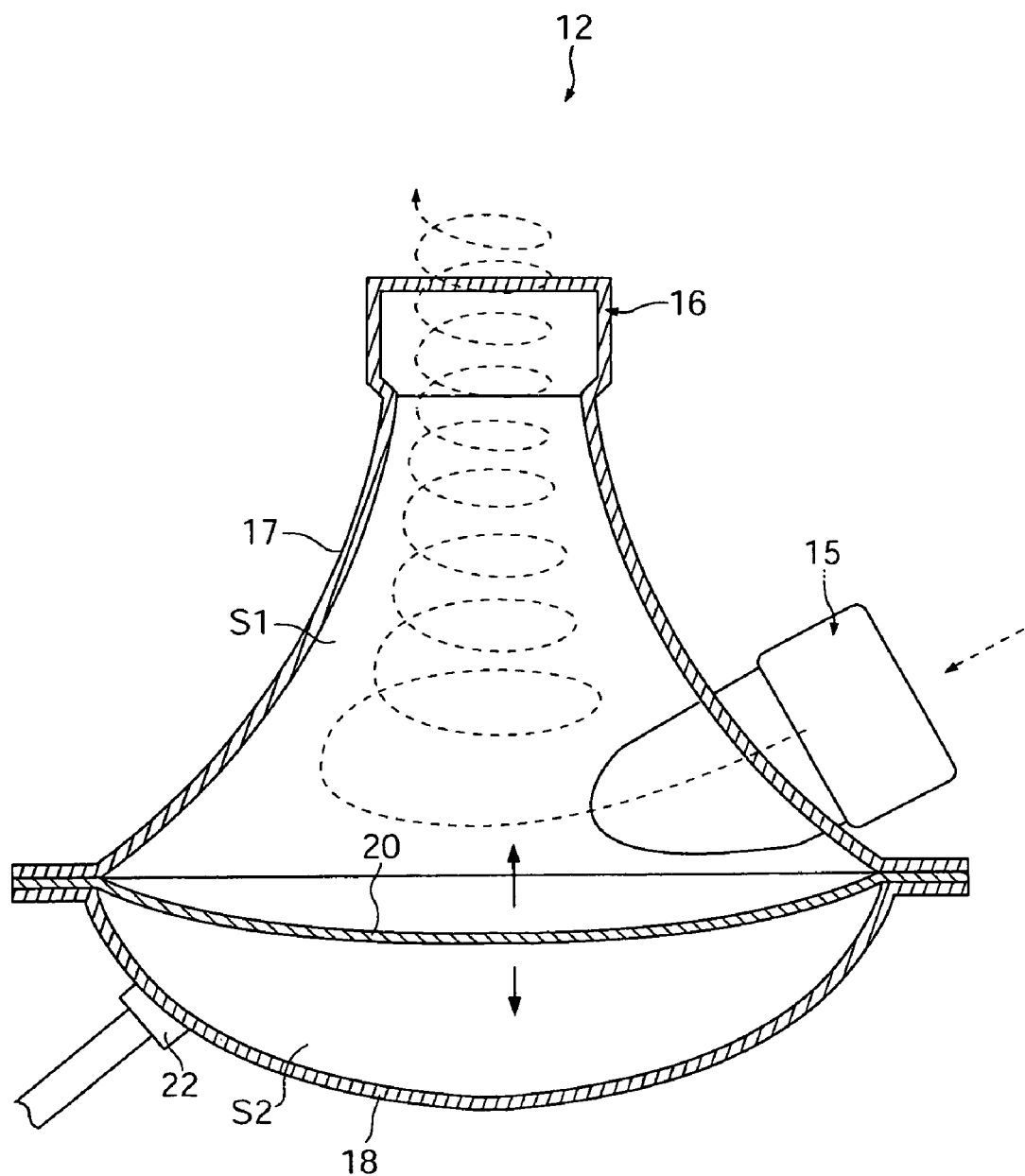
FIG. 2 is a schematic longitudinal sectional view of a driving pump.

The driving pump 12 is a pulsating pump capable of ejecting a pulsatile flow by generating a spiral vortex flow within the pump. More specifically, the driving pump 12, which is shown in FIG. 2, employs the structure that has been already proposed by the present applicant (Japanese Patent Publication No. 2002-167836). To explain more specifically, the driving pump 12 comprises a hollow upper construct 17 of virtually a conical outer shape having a flow-in port 15 and flow-out port 16, a hollow lower construct 18 of virtually a domical outer shape positioned under the upper construct 17, and a flexible diaphragm 20 which partitions the space formed of the constructs 17 and 18 into two, inner spaces S1 and S2. The flow-in port 15, which is shown at the right-end side of FIG. 2, is formed so as to thread through the peripheral wall of the upper construct 17, whereas the flow-out port 16 is provided at the top of the upper construct 17, as shown at the upper end-side of FIG. 2.

The lower construct 18 has a vent hole 22 communicating with the air suction/supply unit 11. Compression air is alternately supplied into and out from the lower inner space S2 on a predetermined timing. When compression air is supplied in and out from the inner space S2, the diaphragm 20 is displaced, increasing or decreasing the volume of the upper inner space S1. As a result, the solution supplied from the flow-out port 16 becomes a pulsatile flow. At this time, a spiral vortex flow is generated in the upper space S1, as indicated by a broken line in FIG. 2. In this state, it is not easy to find a standstill region. In the Examples of the present invention, the pressure (positive pressure) of the air supplied to the inner space S2 is set at about 140 mmHg to 260 mmHg, whereas the pressure (negative pressure) of the air suctioned from the inner space S2 is set at about −30 mmHg to −50 mmHg, however, they are not limited to these values.

As shown in FIG. 1, the circulation channel 13 is formed of a closed loop in such a manner that the solution flows out from the flow-out port 16 of the driving pump 12 and flows in the flow-in port 15 without being exposed to the outside air. To explain more specifically, the flow channel 13 comprises a resistance imparting means 23, which imparts flow resistance to the solution supplied from the flow-out port 16, an upstream-side tube 24 connected to the flow-out port 16, a control tube 25 serving as an amplitude controlling means and connected to the downstream-side end of the upstream-side tube 24, a connection tube 26 connected to the downstream-side end of the control tube 25, a downstream-side tube 27 arranged downstream of the connection tube 26 and connected to the flow-in port 15 of the driving pump 12, and a connection pump 28 provided between the connection tube 26 and the downstream-side tube 27. Note that the members 24 to 28 are connected by known connectors 29. Hereinafter, the portion of the circulation channel 13 upstream of the resistance imparting means 23 is referred to as an "upper line L1" and that downstream of the resistance imparting means 23 is referred to as a "downstream line L2", for convenience's sake.

The resistance imparting means 23 is provided alone in the middle of the connection tube 26 on the assumption of the peripheral resistance of a human body, and constructed of a pinch-form member (not shown) for fastening the connection tube 26. Since the connection tube 26 is fastened by the resistance imparting means 23, if the driving pump 12 pulses, the lowermost blood pressure of the upper line L1 would not reach 0 mm Hg. In this manner, the arterial blood flow of a human body is simulated. The average pulse pressure of the upper line L1 can be adjusted at a predetermined value by controlling the degree of fastening the connection tube 26. In this embodiment, the average pulse pressure is set at about 100 mmHg, which virtually corresponds to the average pulse pressure of a human body. Note that, as the resistance imparting means 23, any type of member including a variable aperture other than the pinch-form member may be used as long as it has the same effect as mentioned above.

The upstream-side tube 24, the connecting tube 26 and the downstream-side tube 27 are formed of vinyl chloride, but not particularly limited thereto. As described later, the retention unit 10B is provided in the middle of the upstream-side tube 24. Since a xenogenic bioprosthetic valve is placed in the retention unit 10B and a check valve 30 is provided in the downstream-side tube 27, the solution can be circulated without a backward flow in the direction indicated by the arrow in the FIG. 1.

The control tube 25 is arranged upstream of the resistant imparting means 23 and serves as a controller for the amplitude of the pulse pressure of the upstream line L1. More specifically, the control tube 25 is formed of a soft material such as segmented polyurethane or silicone, can control the amplitude of the pulse pressure of the upstream line L1 by changing the tube-wall thickness. Note that the amplitude of the pulse pressure of the upstream line L1 is set at, for example, 100 mmHg (average pulse pressure)±20 mm Hg to approximate a human body in this embodiment.

The connection pump 28 is a pulsatile-flow formation pump having the same structure as the driving pump 12. Like reference numerals are used to designate like structural elements corresponding to those of the driving pump 12 and any further explanation is omitted. Note that the connection pump 28 is fitted in such an orientation that the solution flows in through the flow-in port 15 and flows out though the flow-out port 16. The vent hole 22 of the connection pump 28 is open to the outside. The diaphragm 20 is displaced depending upon the solution flow. The solution is loaded in the circulation apparatus 10A in an amount slightly lower than a maximum permissible loading amount of the apparatus 10A. The displacement amount of the diaphragm 20 of the connection pump 28 is slightly lower than a maximum physically permissible displacement amount. By virtue of this, the connection pump 28 gives the damper effect. More specifically, when the solution passes through the connection pump, the diaphragm 20 is displaced, thereby reducing the blood pressure. Accordingly, the connection pump 28 is arranged downstream of the resistance imparting means 23 and serves as a pulse-pressure attenuation means for attenuating the liquid pressure of the solution of the downstream line L2. In this embodiment, the pressure of the solution passed through the connection pump 28 is set at about 10 mm Hg so as to correspond to the pressure of the human left atria.

Note that, the connection pump 28 may be interposed between the control tube 25 and the connection tube 26.

The retention unit 10B, in which the solution flowing through the circulation apparatus 10A is introduced, retains a xenogenic bioprosthetic valve immersed in the solution. In this embodiment, as the xenogenic bioprosthetic valve to be subjected to the cell-removing process and cell-seeding process, a swine aortic valve is used. The retention unit 10B is positioned at a site of the circulation channel 13 having a blood-flow state close to that of the human aortic valve portion. In brief, the retention unit 10B is connected to the middle of the upstream-side tube 24. Hereinafter, for convenience's sake of explanation, the portion of the upstream-side tube 24 upstream of the retention unit 10B is referred to as an inlet-side tube 24A, whereas the portion downstream of the retention unit 10B is referred to as an outlet-side tube 24B. Note that the retention unit 10B may be freely connected to any site of the circulating channel 13 by appropriately selecting the site of the circulation channel 13 whose state (such as pressure) is close to that of the blood flowing through a target living organism tissue.

Figure 3:
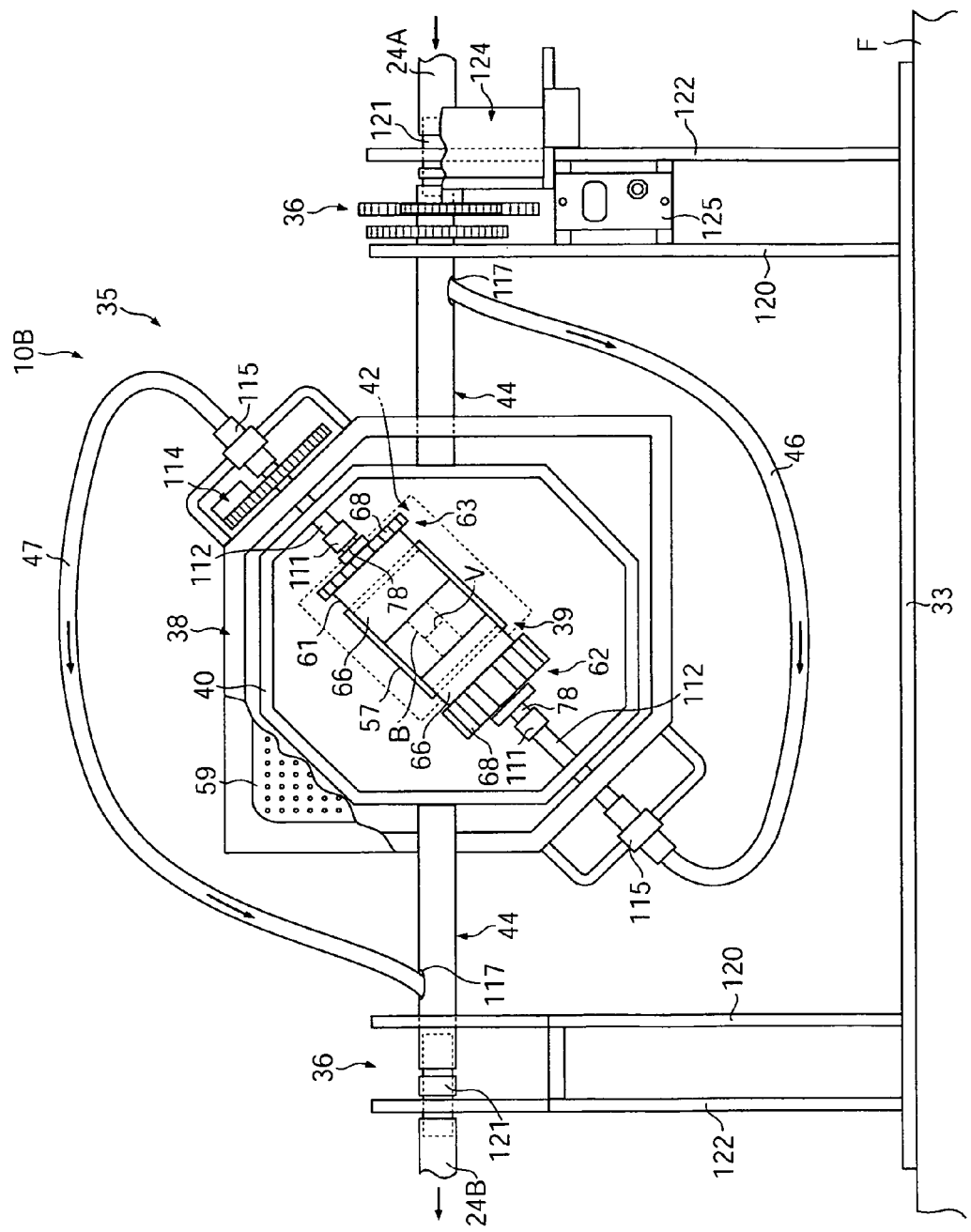
FIG. 3 is a schematic front view of a retention unit constituting the living organism tissue processing apparatus.

As shown in FIG. 3, the retention unit 10B comprises a tabular base 33 capable of being placed on a predetermined surface F, a main body 35 positioned above the base 33, and support members 36, 36 standing at the right and left sides of the base 33 for supporting the main body 35.

The main body 35 comprises a box-form cover 38 having a hexagonal shape as seen from the front, a retention member 39, which is provided within the cover 38, for retaining xenogenic bioprosthetic valve V, a frame member 40 having an octagonal shape (viewed from the front) supporting the retention member 39 and arranged along the inner wall of the cover 38, an irradiation unit 42 (irradiation means), which is provided behind the cover 38, for applying microwave to xenogenic bioprosthetic valve V retained in the retention member 39, supporting shafts 44, 44 respectively extending from the right and left sides of the frame member 40 toward the supporting members 36, 36 through the cover 38, and two tubes, namely, an introduction tube 46 and discharge tube 47, connecting to the retention member 39.

Figure 4:
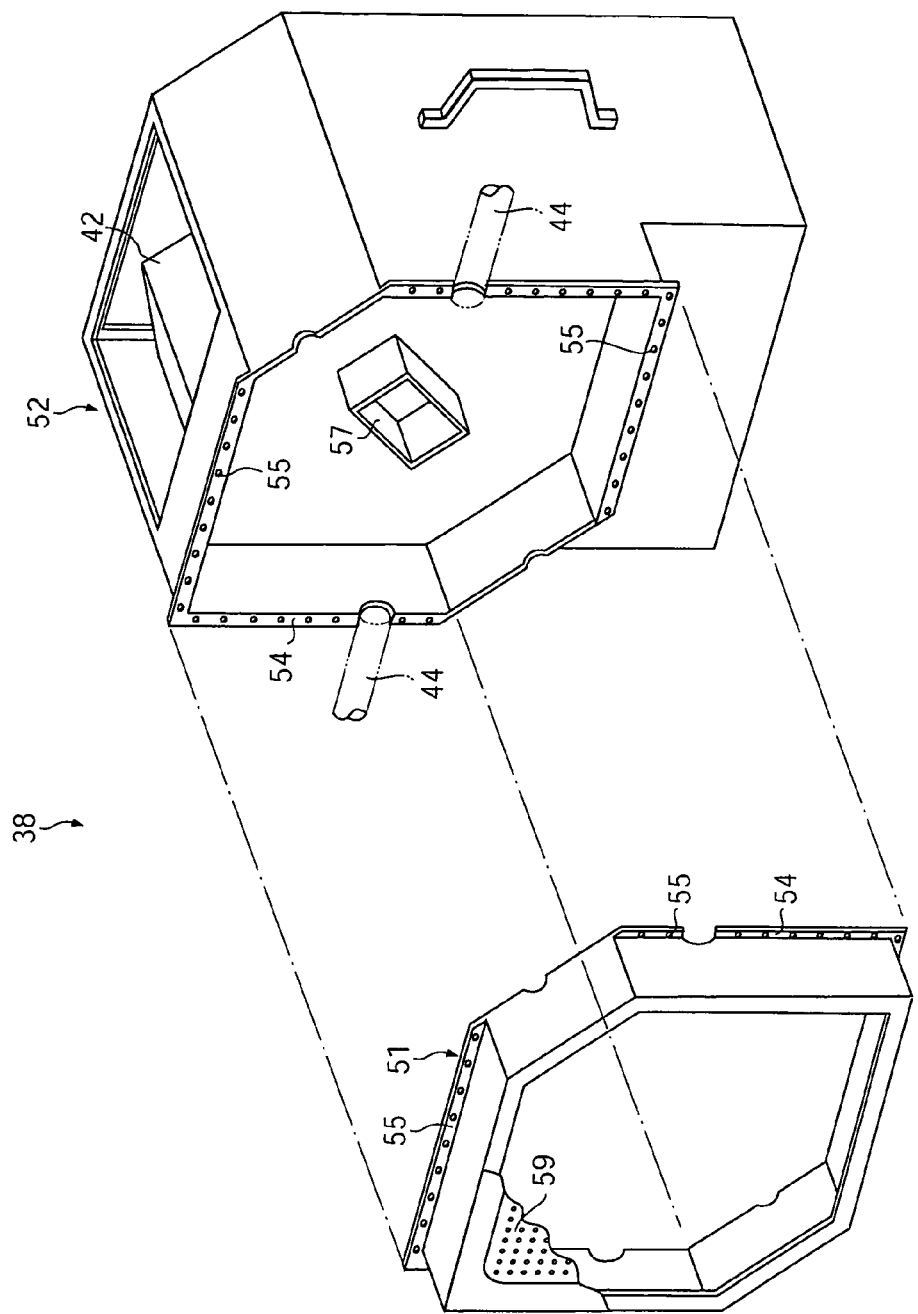
FIG. 4 is an exploded perspective view of a cover of the retention unit.

As shown in FIG. 4, the cover 38 has a box-form structure consisting of two portions longitudinally divided, more specifically composed of a front cover 51 positioned in the front side and a rear cover 52 positioned in the rear side. The butting portion of the front cover 51 and the rear cover 52 is formed at the position crossing with the support shafts 44, 44. In the outer edge portion of the butting portion, flange planes 54, 54 are formed, virtually along the outer edge portion. In the flange planes 54, 54, numerous through-holes 55 for volts (not shown) are formed. When the flange planes 54, 54 are brought in face-to-face contact with each other and united with the volts, the front cover 51 and the rear cover 52 are integrated into one. When the volts are removed from the integrated construct, the front cover 51 can be separated and detached from the rear cover 52. Furthermore, a microwave irradiation port 57 having a square-shape which is open forward is formed around the center of the inside of the rear cover 52. The irradiation port 57 is formed so as to virtually correspond to xenogenic bioprosthetic valve V retained by the retention member 39 frontward (see FIG. 3). With the arrangement, microwave, which is supplied from the irradiation unit 42 rearward, passes through the irradiation port 57 and is applied to xenogenic bioprosthetic valve V within the retention member 39 frontward. Furthermore, the front cover 51 and the rear cover 52 have shapes and structures capable of preventing leakage of the microwave to the outside, when it is applied from the irradiation port 57 toward the retention member 39. Note that, a doorplate 59 is provided at the front end of the front cover 51. The doorplate 59 is formed of a known material through which the state of the retention member 39 can be seen and by which leakage of microwave to the outside can be prevented.

Figure 5:
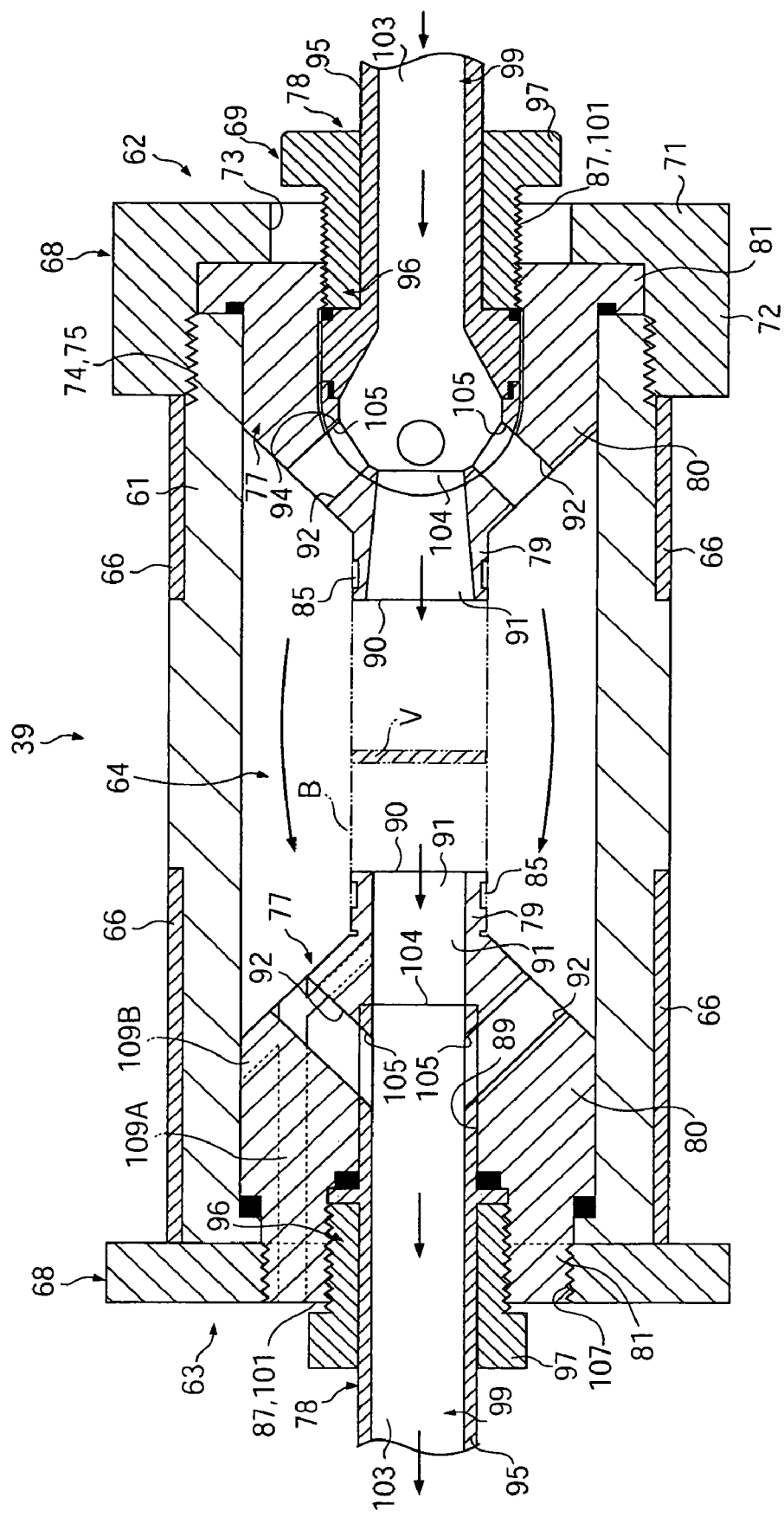
FIG. 5 is a schematic sectional view of the retention member.

As shown in FIG. 5, the retention member 39 comprises an acrylic cylindrical member 61 extended in right and left directions in the figure, a flow-in portion 62 positioned at the right end side of the cylindrical member 61, a flow-out portion 63 positioned at the left end side thereof, and an installation space 64 for xenogenic bioprosthetic valve V between the flow-in portion 62 and the flow-out portion 63. In the retention member 39, the solution flows into the cylindrical member 61 from the flow-in portion 62, passes through the installation space 64 and flows out from the flow-out portion 63 to the outside, as described later.

The cylindrical member 61 has open each ends in the extending direction. At the open ends, the flow-in portion 62 and the flow-out portion 63 are set. A thin aluminium plate 66 is adhered to the entire outer circumferential surface of the cylindrical member 61 except for the center portion virtually corresponding to the installation space 64. With this structure, microwave supplied from the irradiation unit 42 (see FIG. 3)

transmits only through the center circumferential-wall region of the cylindrical member 61 virtually corresponding to the installation space 64. As a result, the microwave can be converged to the center region; at the same time, an increase in temperature of the outside portion of the installation space 64 can be prevented.

Figure 6:
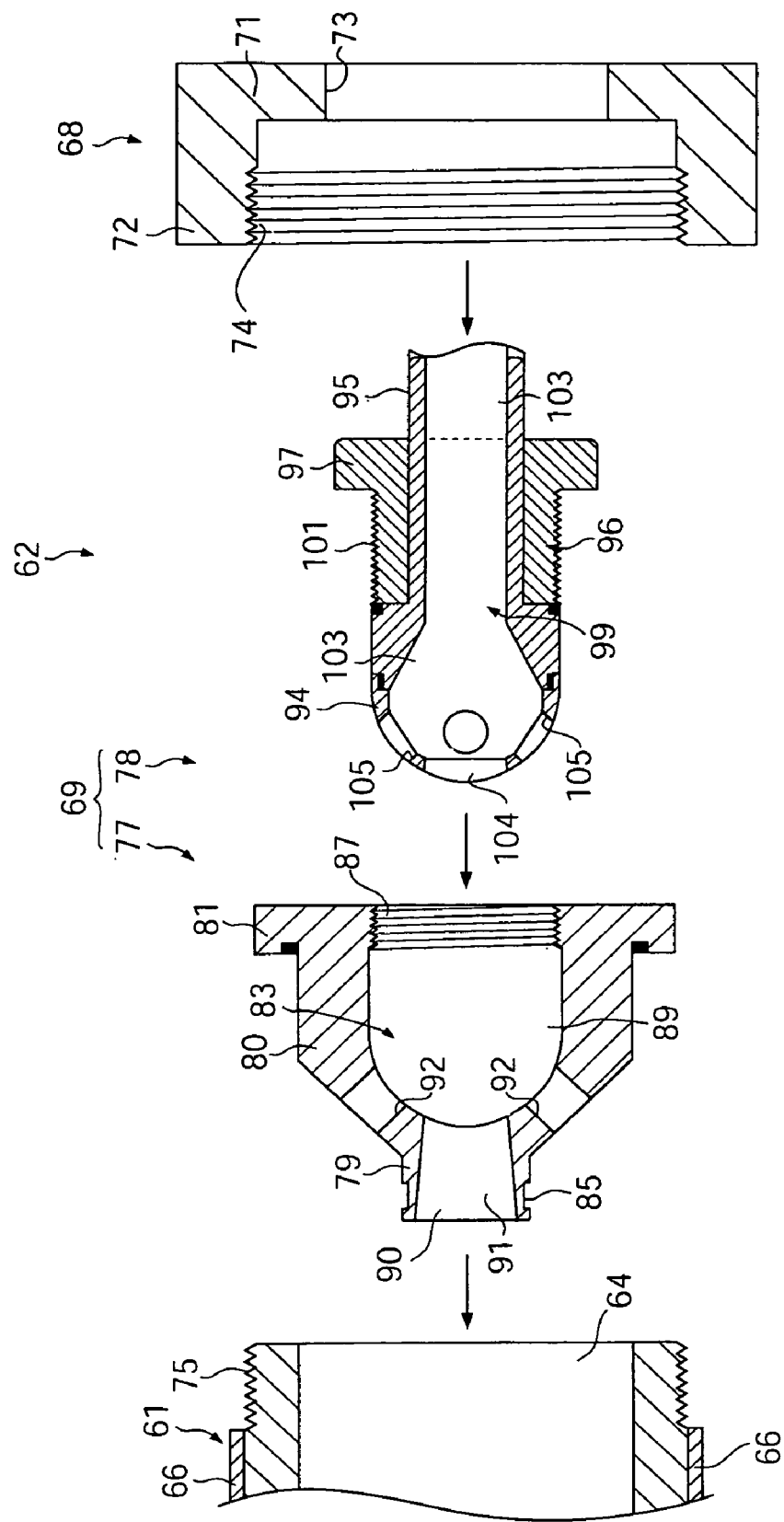
FIG. 6 is an exploded sectional view of the right-hand side of the structure in FIG. 5.

As shown in FIGS. 5 and 6, the flow-in portion 62 comprises an end member 68 engaged with the outer circumferential surface of the cylindrical member 61, and a channel formation member 69 positioned within the end member 68.

The end member 68 is formed like a container with the bottom having an opening at the left side in the FIG. 6. More specifically, the end member 68 has a bottom wall 71 positioned at the right side of the figure and a side wall 72 continuously formed to the circumferential edge side of the bottom wall 71 and extending virtually perpendicularly (toward the left in FIG. 6) to the bottom wall 71. The bottom wall 71 has a through-hole 73 at about the center. The sidewall 72 has a screw thread 74 formed in the inner circumferential of the opening side. The screw thread 74 is to be engaged with a screw thread 75 formed in the outer circumferential of the cylindrical member 61.

Figure 7:
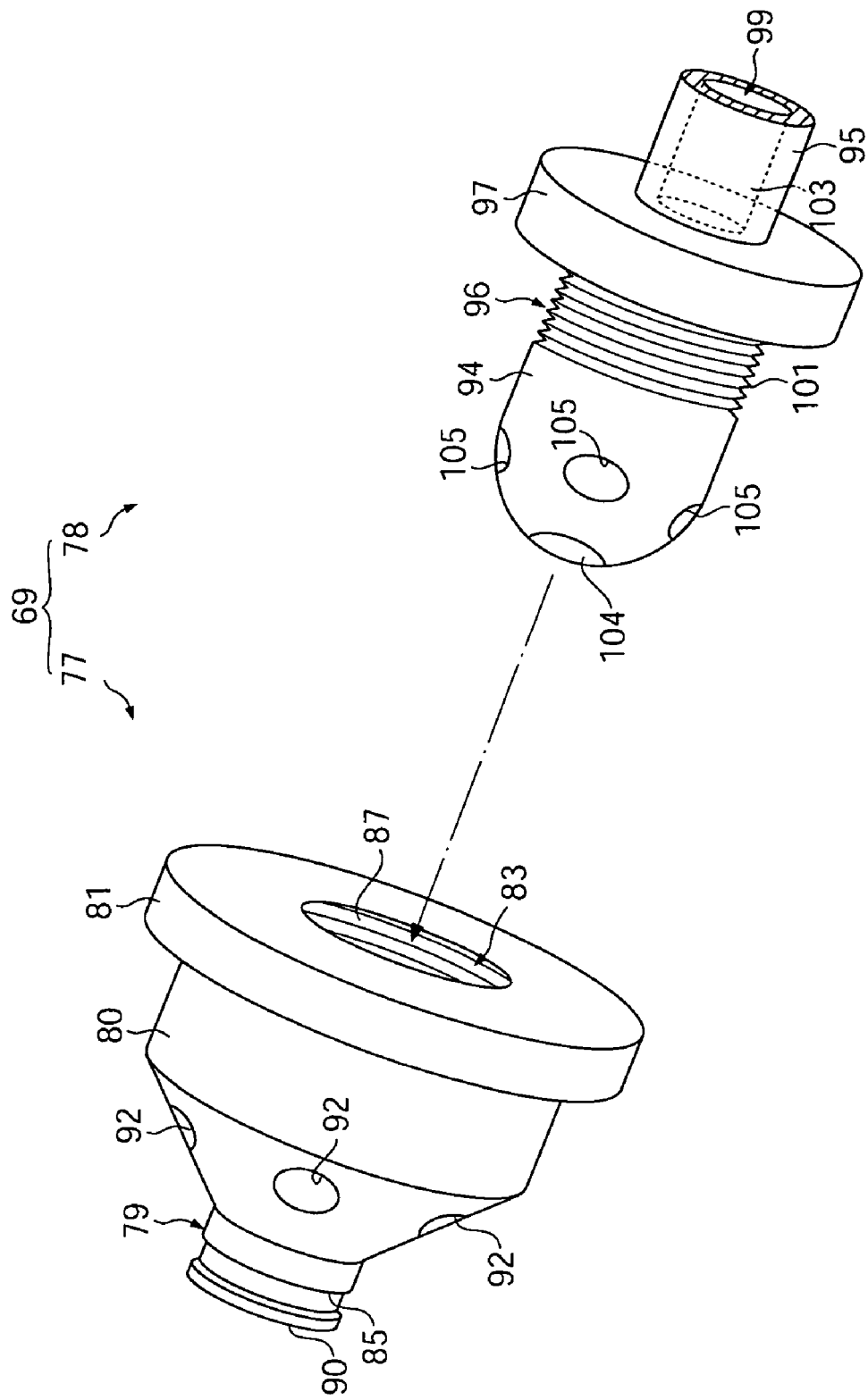
FIG. 7 is a schematic exploded perspective view of a channel formation member of a flow-in port.

As shown in FIGS. 5 to 7, the channel formation member 69 comprises a hollow conical pipe 77 having an analogous shape to a cone, and an insertion pipe 78 to be inserted into the conical pipe 77.

The conical pipe 77 comprises a cylindrical top portion 79 positioned near the installation space 64, a skirt-form portion 80 which gradually expands outwardly from the top portion 79 to the right side of the FIG. 6 and starts, at the middle, extending linearly from the right and left direction in the figure, and a flange-form hem portion 81 continuously formed at the right end side of FIG. 6 of the skirt-form portion 80, and inner space 83 formed within the portions 79 to 81 and communicating with the outside at the right and left side in the FIG. 6. Note that, in the section explaining the channel formation member 69 below, if not otherwise specified, the term "leading edge side" refers to the side of the conical pipe 77 close to the top portion 79 and the term "back end side" refers to the side of the conical pipe 77 close to the hem portion 81.

On the outer circumferential surface of the top portion 79, a stopper groove 85 is formed along the circumference. When the end portion of a swine blood-vessel tissue B containing the aortic valve (as a xenogenic bioprosthetic valve V) is placed over the stopper groove 85 and clamped with a binding member (not shown), as shown in FIG. 5, removal of the blood-vessel tissue B from the top portion 79 can be restricted.

In the skirt-form portion 80, the outer diameter of the hem portion 81 is set equal to the inner diameter of the cylindrical member 61 such that the hem portion 81 can be just fit within the cylindrical member 61.

The hem portion 81 is formed in a ring form. The outer diameter of the hem portion 81 is set equal to the inner diameter of the sidewall 72 of the end member 68. With this structure, the hem portion 81 can be just fit within the end member 68. In the inner circumferential surface of the hem portion 81, a screw thread 87 is formed.

The inner space 83 has an opening portion at the right-end side in the FIG. 6. The inner space 83 comprises a basal space 89 to which the tip portion of the insertion pipe 78 is to be inserted through the opening portion, a main channel 91 communicating with the basal space 89 and extending toward an opening portion 90 formed at the leading edge side, and four side channels 92 provided around the main channel 91 and communicating with the basal space 89. The basal space 89 has the inner space whose shape agrees with the top portion of the insertion pipe 78, can just fit the insertion pipe 78. The main channel 91 is formed like a taper-hole whose inner diameter is reduced inward from the top portion 79, but not limited to this. The side channel 92 is formed in the inclined surface of the skirt-form portion 80, as shown in FIG. 7. More specifically, four side channels 92 are arranged at equal intervals along circumference direction in the skirt portion 80. It should be noted that the total area of the opening portions of the side channels 92 is set equal to that of the main channel 91, in this embodiment.

As shown in FIG. 6, the insertion pipe 78 comprises a spherical portion 94 having a spherical outer shape at the leading edge side, a cylindrical portion 95 having a smaller outer diameter than that of the spherical portion 94 and continuously formed to the spherical portion 94 via a step portion, an external cylinder portion 96 fitting around the outer circumferential surface of the cylindrical portion 95 so as to be mutually rotatable, a ring-form collar portion 97 continuously formed to the back end side of the external cylinder portion 96 and having an outer diameter smaller than the inner diameter of the through hole 73 of the end member 68, and an inner space 99 formed within the spherical portion 94 and the cylinder portion 95. In the outer circumferential surface of the external cylinder portion 96, a screw thread 101 is formed. The screw thread 101 is engaged with the screw thread 87 formed in the inner portion of the hem portion 81. With this structure, the insertion pipe 78 can be attached to the conical pipe 77.

The inner space 99 comprises a basal channel 103 through which the solution flows, a top hole 104 communicating with the basal channel 103 and opened at the leading edge side of the spherical portion 94, and four side holes 105 formed around the top hole 104 and communicating with the basal channel 103. When the leading edge side of the insertion pipe 78 is fit in the inner space 83 of the conical pipe 77, the top hole 104 comes to constantly communicate with the main channel 91. The side holes 105 are arranged virtually at equal intervals along the circumference direction in the surface of the spherical portion 94. When the insertion pipe 78 is fit in the conical pipe 77, the side holes 105 can rotatably change the positions from a maximum communication position at which they can completely communicate with all side channels 92 to a shut-off position at which the communication with all side channels 92 is completely shut off by mutually rotating the pipes 78 and 77. The insertion pipe 78 thus controls a flow amount by changing its position from the site at which the total flow amount of the solution flowing out from all side channels 92 is equal to that flowing out from the main channel 91, to the site at which the total flow amount of the solution flowing out from all of the side channels 92 is virtually zero. In this sense, the insertion pipe 78 acts like a variable throttle, which controls the flow amount of the solution flowing out from the side channels 92.

Figure 8:
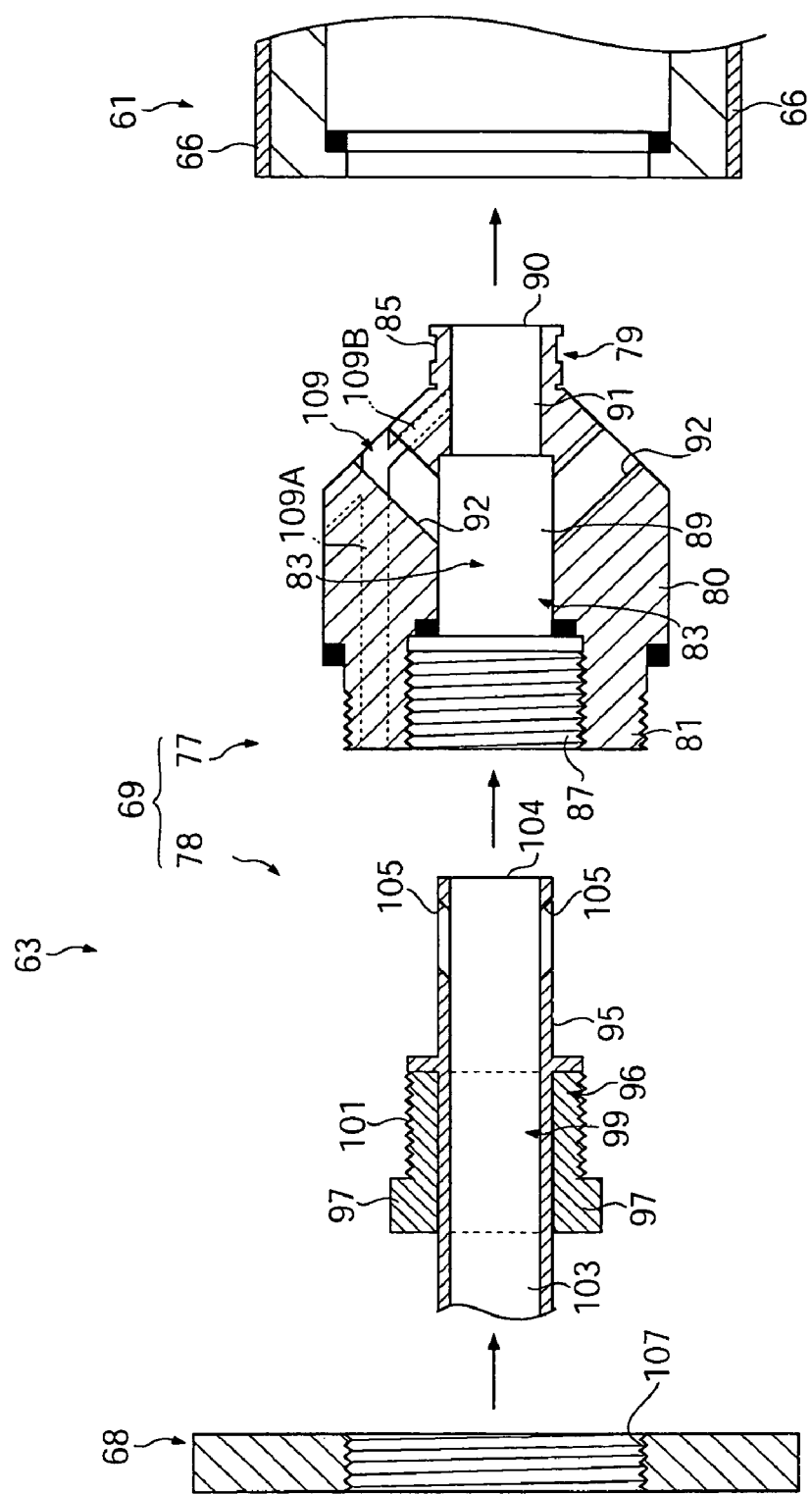
FIG. 8 is an exploded sectional view of the left-hand side of the structure in FIG. 5.
Figure 9:
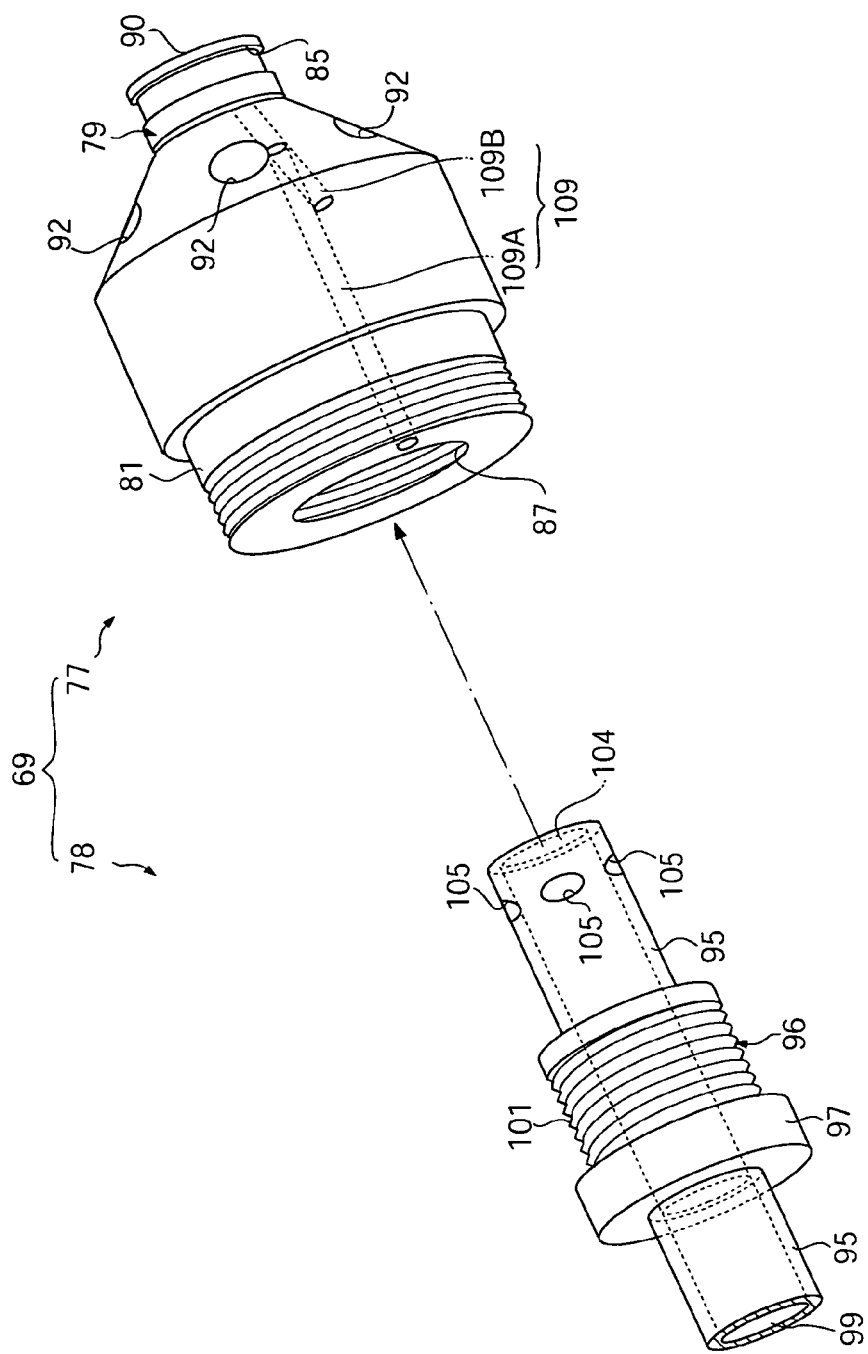
FIG. 9 is a schematic exploded perspective view of a channel formation member of a flow-out port.

As shown in FIGS. 5, 8 and 9, the flow-out portion 63 partly differs in shape from the flow-in portion 62; however, has substantially the same structural elements and functions in a virtually similar manner.

Therefore, like reference numerals are used in the flow-out portion 63 to designate the same or equivalent structural elements of the flow-out portion 63 corresponding to those of the flow-in portion 62 and any further explanation is omitted or simplified. Only the difference from the flow-in portion 62 will be supplementarily explained.

The end member 68 of the flow-out portion 63 is formed like a nut. Virtually at the center of the end member 68, a screw hole 107 is provided so as to extend in the right and left direction in the FIG. 8.

The conical pipe 77 of the flow-out portion 63 differs from that of the flow-in portion 62 in shape of the hem portion 81 continuously formed to the skirt-form portion 80. Specifically, the hem portion 81 is formed like a screw cylinder having an outer diameter smaller than the largest outer diameter of the skirt-form portion 80. The outer circumferential portion of the hem portion 81 is engaged with the screw hole 107 of the end member 68. The conical pipe 77 has a guide channel 109 for inserting a thermo-sensor (not shown) therein. The guide channel 109 is formed outside the inner space 83. The channel 109 comprises a first guide channel 109A extending from the back end side of the hem portion 81 to the inclined surface the skirt-form portion 80 and a second guide channel 109B branched in the middle of the first guide channel 109A and extending toward the main channel 91. Note that two or either one of the guide channels 109A and 109B may be omitted.

The insertion pipe 78 of the flow-out portion 63 differs from that of the flow-in portion 62 in its entire shape. In the insertion pipe 78, the cylindrical portion 95 is extended toward the leading edge side in place of the spherical portion 94. The top hole 104 is formed at the leading edge side of the cylindrical portion 95. Four side holes 105 are provided virtually at equal intervals along the circumference direction in the outer circumferential surface of the leading edge side of the cylindrical portion 95.

Note that blacked out members in FIGS. 5, 6 and 8 are O rings for sealing.

As shown in FIG. 3, the frame member 40 supports the retention member 39 so as to rotate therein. More specifically, the insertion pipes 78, 78 protruding outward virtually from the center of the end members 68, 68 are connected to rotation pipes 112, 112 via pipe nuts 111, 111. The rotation pipes 112, 112 pass through bearings (not shown) each attached to part of the frame member 40 and protrude out of the frame member 40. The retention member 39 is fit within the frame member 40 such that the rotation pipes 112, 112 can obliquely extend at an angle of 45°, as shown in the FIG. 3. The retention member 39 can be rotated (self-rotated) around on the rotation pipes 112, 112. In the outer surface of the frame member 40 and near a site from which the rotation pipe 112 at the side of the flow-out portion 63 (the upper right of the FIG. 3) protrudes, a self-rotation driving means 114 having a motor and gear, etc., is provided. The retention member 39 is rotated within the frame member 40 by actuating the self-rotation driving means 114. Furthermore, the rotation pipes 112, 112 are connected to the introduction tube 46 and discharge tube 47, respectively, via rotation joints 115 fixed to the structure placed near the frame-member 40. As the rotation joint 115, a known joint is used which connects two types of pipe-form members (rotation pipes 112, 112 and tubes 46, 47) while allowing mutual rotation and mutual communication. By virtue of the joint, even if the rotation pipes 112, 112 are rotated by operation of the self-rotation driving means 114, the rotation force does not transmit to each of tubes 46 and 47.

The irradiation unit 42 is a known unit using a magnetron (not shown) as a source of microwave. Detailed explanation of the unit is omitted herein.

The support shaft 44 is a hollow pipe and houses the end portions of the introduction tube 46 and the discharge tube 47 therein. To explain more specifically, a slot hole 117 is formed at a position of the outer circumferential surface of each of the support shafts 44, 44 within and in the vicinity of the support members 36, 36. Into the slot holes 117, the tubes 46 and 47 extending from the rotation pipes 112, 112 are inserted.

Figure 10:
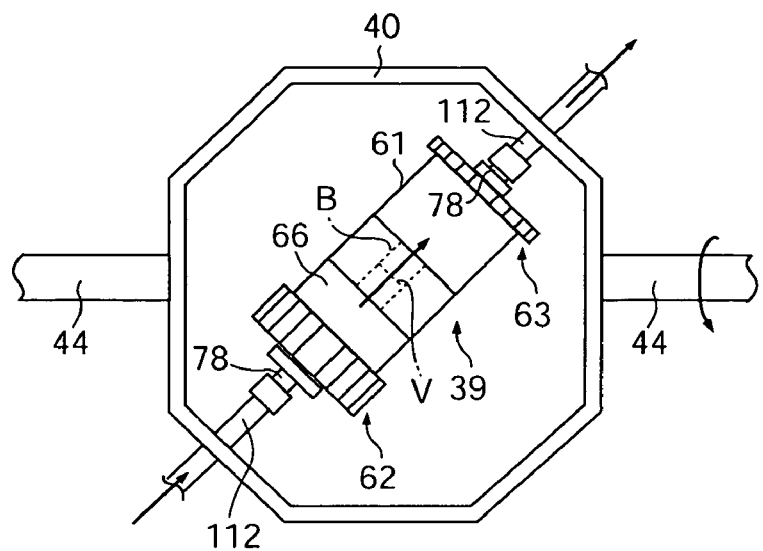
FIG. 10(A) is a view of a part extracted from the structure of FIG. 3 including the retention member.
FIG. 10(B) is the same structure shown in FIG. 10(A) in the state of rotating by 180° about a support shaft from the state shown in FIG. 10(A)
Figure 10:
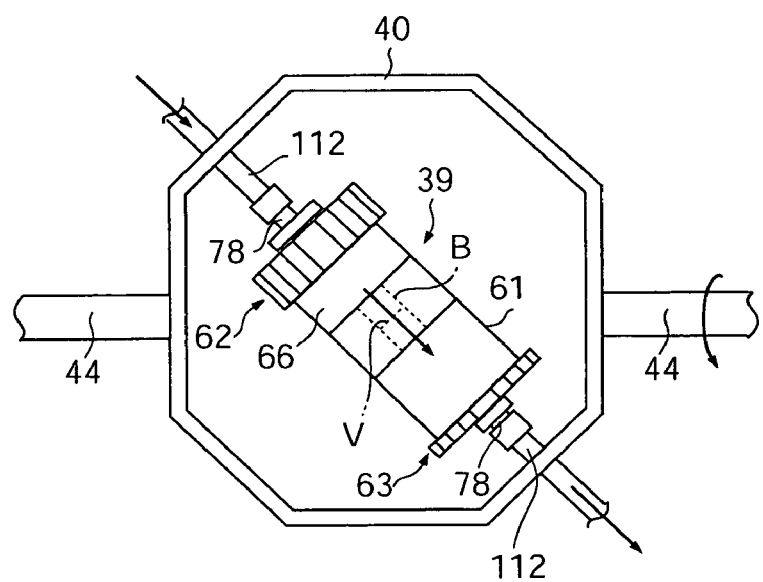

The support member 36 comprises a first support portion 120 arranged at the inner side for rotatably supporting the support shafts 44, 44, and a joint support portion 122 arranged outside the first support portion 120 for supporting a rotation joint 121 having the same structure as that of the rotation joint 115 mentioned above. The rotation joint 121 supported by the support member 36 (at the left side in FIG. 3) connects the discharge tube 47 inserted in the support shaft 44 at the left side and the outlet-side tube 24B, mutually rotatably. On the other hand, the rotation joint 121 supported by the support member 36 (at the right side in FIG. 3) connects the introduction tube 46 inserted in the support shaft 44 at the right side and the inlet-side tube 24A, mutually rotatably. Furthermore, at the support member 36 (at the right side in FIG. 3), a revolution driving means 124 having a motor and a gear, etc., is provided. The support shafts 44, 44 can be rotated by operating the revolution driving means 124. As mentioned above, when the support shafts 44, 44 rotate, the frame member 40 and the retention member 39 simultaneously rotate (revolve) around on the support shafts 44, 44. The introduction tube 46 and the discharge tube 47 inserted in the support shaft 44, each are designed not to interfere with the base 33 during the revolution. More specifically, they have an appropriate length and are arranged so as to pass through the space between the base 33 and the support shaft 44. As shown in FIG. 10, when the support shaft 44 is revolved by 180° (half rotation) from the state shown in FIG. 10(A), the frame member 40 is rotated. As a result, up/down and right/left of the retention member 39 are inverted, as shown in FIG. 10(B). More specifically, the retention member 39 can be not only self-rotated by the self-rotation driving means 114 but also revolved by the revolution driving means 124. When the retention member 39 revolves, the up/down and right/left of blood-vessel tissue B are inverted. Note that reference numeral 125 in FIG. 3 indicates a switch for the revolution driving means 124. Note that a cooling means may be provided for cooling the periphery of the introduction tube 46 to prevent the temperature of the solution from increasing.

Next, procedure for setting up xenogenic bioprosthetic valve V in the retention unit 10B constructed above and function of the retention unit 10B during the set-up time will be described below.

First, from the state shown in FIG. 3, the rotation pipe 112 is released from the rotation joint 115. Then the pipe nut 111 is loosen by turning it and removed from the retention member 39, thereby removing the retention member 39 from the rotation pipes 112, 112. Thereafter, the end members 68, 68 are removed, and then the flow-in portion 62 and flow-out portion 63 are removed from the cylindrical member 61. Subsequently, while keeping the state where the top portion 79, 79 of the flow-in portion 62 and the top portion 79 of the flow-out portion 63 are allowed to face as shown in FIG. 5, both ends of swine blood-vessel tissue B containing aortic valve V are inserted to the top portions 79, 79, respectively and then, clamped by binding members (not shown) on the stopper grooves 85, 85, respectively. Blood-vessel tissue B is set in such an orientation that the solution is allowed to flow through aortic valve V (uni-direction valve) from the right side to the left side in FIG. 5. Thereafter, the flow-in portion 62 and the flow-out portion 63 connected by way of blood-vessel tissue B are returned again in the cylindrical member 61, and the end members 68, 68 are attached to the cylindrical member 61, and further the retention member 39 is fit to the rotation pipes 112, 112 as shown in FIG. 3. In this manner, the setup of blood-vessel tissue B is completed.

In the cell-removing process, the cell-removing solution is supplied from the introduction tube 46 to the insertion pipe 78 of the flow-in portion 62 by way of the rotation pipe 112. At this time, the insertion pipes 78, 78 of the flow-in portion 62 and flow-out portion 63 are set at the positions where the side holes 105 and the side channels 92 of conical pipe 77 are completely communicable, as shown in FIG. 5. With this arrangement, the cell-removing solution supplied to the flow-in portion 62 enters blood-vessel tissue B by ways of the top hole 104 and the main channel 91 of the flow-in portion 62, passes through aortic valve V, and goes to the main channel 91 of the flow-out portion 63. Simultaneously, the same amount of the solution flows through the side holes 105 and sub channels 92 of the flow-in portion 62, passes through the inner space of the cylindrical member 61 and goes into the side channel 92 of the flow-out portion 63, so as to detour blood-vessel tissue B. The cell-removing solution passed through the main channel 91 and the side channels 92 of the flow-out portion 63 flows out from the insertion pipe 78 of the flow-out portion 63 and is discharged to the discharge tube 47 through the rotation pipe 112, as shown in FIG. 3. Therefore, the main channel 91 and the top hole 104 provided in each of the flow-in portion 62 and flow-out portion 63 constitute a first channel mutually communicating through the tubular living organism tissue (blood-vessel tissue B), whereas the side channels 92 and the side holes 105 provided in each of the flow-in portion 62 and the flow-out portion 63 constitute a second flow channel mutually communicating through the detour root formed outside of the living organism tissue (blood-vessel tissue B).

In performed the cell-removing process mentioned above, the irradiation unit 42 and the self-rotation driving means 114 are operated. The retention member 39 is self-rotated while applying microwave to blood-vessel tissue B retained in the retention member 39. By this operation, the cell removing operation can be applied uniformly in the entire circumference direction of blood-vessel tissue B. The cell removing operation is preferably performed while checking the temperature of the solution in and out of blood-vessel tissue B by using thermo-sensors (not shown) inserted in the first and second guide channels 109A, 109B (see FIG. 5). In this case, the cell-removing solution is allowed to flow virtually at the same flow rate inside and outside the blood-vessel tissue B so that there is no temperature difference between them. The temperature difference between them can be checked by use of the thermo sensors (not shown) inserted in the first and second guide channels 109A and 109B. Note that when the temperatures of the inside and outside reach human body temperature (e.g., 37° C.), the irradiation unit 42 automatically stops irradiation of microwave, whereas it automatically starts irradiation of microwave when the temperatures become lower than the body temperature. The irradiation unit 42 of this embodiment can apply a microwave having a frequency of 2.45 GHz and a power of about 0 to 1200 W. Note that the temperature sensor may be introduced into the first channel from a hole formed in the middle of the discharge tube 47.

On the other hand, in performing the cell-seeding process, application of microwave by the irradiation unit 42 and the self-rotation of the retention member 39 are stopped. The insertion pipes 78, 78 within the retention member 39 are changed in position by turning and loosening the collar portion 97 and rotating the cylindrical form portion 95, from the state shown in FIG. 5 to the state where the communication between the side holes 105 (see FIG. 5, etc.) and the side channels 92 is completely shut off. Thereafter, the cell-containing solution is supplied to the insertion pipe 78 of the flow-in portion 62. The cell-containing solution then passes through the top hole 104 of the flow-in portion 62 and the main channel 91, reaches blood-vessel tissue B, passes through aortic valve V, flows into the main channel 91 of the flow-out portion 63, and is then discharged from the insertion pipe 78 of the flow-out portion 63. During this operation, the insertion pipes 78, 78 are placed in the position at which communication between the side channels are shut off. Therefore, the cell-containing solution would not flow outside blood-vessel tissue B, unlike the case of cell-removing process mentioned above.

In performing the cell-seeding process, the revolution driving means 124 shown in FIG. 3 is actuated. The retention member 39 rotates together with the frame member 40 around on the support shafts 44, 44, with the result that the retention member 39 is rotated upside down in the direction indicated in FIG. 10. Since the retention member 39 revolves, the autologous cells of the cell-containing solution can be attached uniformly to blood-vessel tissue B without gravitational effect.

Next, methods of removing and seeding cells by use of the living organism tissue processing apparatus 10 will be described with reference to FIG. 1, etc.

First, blood-vessel tissue B including aortic valve V is taken from an animal such as a pig. Blood-vessel tissue B is set in the retention unit 10B in the manner as mentioned above. The cell-removing solution is injected into the living organism tissue processing apparatus 10, and then circulated. As the cell-removing solution, a surfactant such as deoxycholic acid (bile acid), sodium dodecyl sulfate (SDS), or Triton X-100 were used. At this time, the cell-removing solution is circulated in the living organism tissue processing apparatus 10 while keeping the state of the solution close to that of the human blood flow, in the manner mentioned below.

When a switch (not shown) is pressed, the suction/supply unit 11 shown in FIG. 1 is actuated. Then, the cell-removing solution is circulated through the circulation channel 13 by pulsation of the driving pump 12. More specifically, the cell-removing solution ejected from the driving pump 12 flows through the upstream line L1 at the pressure virtually corresponding to a general aortic pressure of a human body, passes through the retention unit 10B arranged in the middle of the upstream line L1, and reaches to the resistance imparting means 23 for imparting the resistance corresponding to the peripheral resistance of a human body. The cell-removing solution coming out of the resistance imparting means 23 passes through the connection pump 28 and flows into the driving pump 12 at a pressure of about 10 mm Hg virtually corresponding to left atrial pressure.

At this time, in the retention unit 10B, the cell-removing solution flows through both inside and outside of blood-vessel tissue B retained in the retention member 39 at the flow state corresponding to the blood flow flowing through the aorta of a human body; at the same time, microwave is applied to blood-vessel tissue B which is being rotated by self-rotation of the retention member 39 as mentioned above. In this manner, various types of original cells (endothelial cells, fibroblast cells, smooth muscle cells) are removed from blood-vessel tissue B taken from an animal. As a result, a substrate formed of collagen alone remains. In this embodiment, the microwave is specified to have a frequency of 2.45 GHz, and a power of about 100 W to 500 W, but not limited to these conditions. However, the power of the microwave can be changed within a predetermined range as long as the microwave does not produce any denaturation (harmful a human body) of blood-vessel tissue B and can produce a predetermined cell-removing effect. Alternatively, electromagnetic wave different in frequency and acoustic wave may be applied. Furthermore, the flow of the cell-removing solution may well if it is not analogous to the blood flow. In other words, a pulsatile flow may be accepted.

After the cell-removing solution is discharged from the living organism tissue processing apparatus 10, normal saline solution is injected into the living organism tissue processing apparatus 10. After the apparatus 10 is washed by circulating the normal saline solution, the normal saline solution is discharged from the living organism tissue processing apparatus 10. Subsequently, a binder such as fibronectin is directly injected into the first channel of the retention member 39 to block the open ends of the flow-in portion 62 and the flow-out portion 63. In this manner, blood-vessel tissue B from which cells have been removed and retained in the retention member 39 is immersed in the binder for a predetermined time. Thereafter, the binder is discharged from the retention member 39 and the cell-containing solution is injected into the retention member 39. The cell-containing solution is prepared by taking autologous cells (endothelial cells, fibroblast cells and/or smooth muscle cells) of a recipient, culturing for a predetermined time, and adding to a predetermined culture solution. As the culture solution, any culture solution may be used as long as it can be used for the cell-seeding process. Examples of such a culture solution include M199 (Medium 199, manufactured by the company Life Technologies). In the same manner as in the case of the binder, blood-vessel tissue B from which cells have been removed is immersed in the cell-containing solution for a predetermined time, and then, the circulation apparatus 10A is actuated to circulate the cell-containing solution in the living organism tissue processing apparatus 10 at the flow state corresponding to the blood flow of a human body. In this manner, blood-vessel tissue B from which cells have been removed is placed in the cell-containing solution flowing at the flow state corresponding to the blood flow through the human aorta, autologous cells are seeded in the blood vessel tissue B. The revolution driving means 124 (see FIG. 3) is actuated before the pulsatile flow is generated by the circulation apparatus 10A. In this way, blood-vessel tissue B immersed in the cell-containing solution is rotated upside down, thereby uniformly attaching the cell-containing solution to virtually entire region of blood-vessel tissue B without gravitational effect. Note that such a revolution operation may be continuously performed during the time when pulsatile flow of the cell-containing solution is generated.

According to such an embodiment, the cell-removing effect and the cell-seeding effect can be significantly enhanced; at the same time, the cell-removing process and the cell-seeding process can be performed in a sequence of operations while retaining blood-vessel tissue B in the retention member 39. The processing of a xenogenic bioprosthetic valve involved in transplant can be simply performed in a short time. In addition, since such a sequence of operations can be performed in a single airtight channel, the xenogenic bioprosthetic valve can be kept clean while preventing pollution.

Next, the present inventors performed experiments for demonstrating the cell-removing effect and cell-seeding effect based on this invention.

(1) Experiment of Cell-Removing Effect

Example 1

In Example 1, bile acid of 37° C. was used as a cell-removing solution. The bile acid was injected into the circulation apparatus 10A and allowed to flow so as to correspond to the human blood (pulsatile flow) in the aorta. A swine blood-vessel tissue containing the aortic valve was allowed to leave alone in the flow for 24 hours. At this time, the circulation apparatus 10A was operated under conditions: an average flow rate: 5 L/minute, a pulsating rate (beating rate) of the driving pump 12: 70 times/minute, an average liquid pressure of the bile acid: about 90 mmHg where the maximum and minimum pressures of the liquid were allowed to correspond to the maximum and minimum pulse pressures of a typical person, respectively. After treatment, the blood-vessel tissue was observed under a microscope and the magnified view was taken by a camera. Original cells (endothelial cell and fibroblast cells) remaining in the blood-vessel tissue were counted to obtain an average number of original cells per unit area (1 mm$^2$).

As a result, about 850 original cells per unit area remained as shown in FIG. 11.

Example 2

In Example 2, a predetermined microwave was applied to a blood-vessel tissue while rotating by the retention unit 10B in addition to the conditions of Example 1. The microwave having a frequency of 2.45 GHz was used herein and applied under the following three different conditions by varying power and irradiation time: a power of 100 W for 8 hours, a power of 500 W for 12 hours, and a power of 500 W for 24 hours. In all cases, the blood-vessel tissue was rotated 4 times per minute in a self-rotation manner. Original cells remaining in the blood-vessel tissue were counted in the same manner as in Example 1 and an average cell number per unit area (1 mm$^2$) was obtained.

As a result, about 380 original cells remained per unit area when microwave was applied at a power of 100 W for 8 hours. On the other hand, in the cases where microwave was applied at a power of 500 W for 12 hours and 24 hours, no original cells were observed to remain. In addition, the protein contained in the original tissue was virtually removed. In all cases, collagen and elastin were not virtually affected.

Comparative Example 1

An experiment was performed as a Comparative Example to Examples 1 and 2. A blood-vessel tissue as used in Example 1 was immersed in bile acid standing still in a container for 24 hours. Original cells remaining in the blood-vessel tissue were counted to obtain an average number of original cells per unit area (1 mm$^2$) in the same manner as in Example 1.

As a result, about 970 of original cells per unit area remained as shown in FIG. 11.

About 1880 original cells per unit area (1 mm$^2$) were present in the blood-vessel tissue used in Examples 1 and 2 and Comparative Example 1 in the initial conditions before subjecting to a cell-removing process.

From the results, it is clear that the number of original cells removed in Examples 1 and 2 is significantly larger than that of Comparative Example 1. Thus, high cell-removing effect is demonstrated. In particular, when the case where the blood-vessel tissue is simply immersed in a pulsatile flow of bile acid (Example 1) is compared to the case where irradiation of microwave is further performed besides the immerse treatment, the cell-removing effect is higher in the latter case. When a frequency of microwave is increased from 100 W to 500 W, original cells cannot remain. Note that although detailed description was omitted herein, microwave as mentioned above can be applied to the blood-vessel tissue immersed in bile acid allowed to stand still. The cell-removing effect of this case is higher than that of Comparative Example 1.

(2) Experiment for Cell-Seeding Effect

Example 3

In Example 3, after the cell-removing process, the blood-vessel tissue was washed with normal saline solution for about one hour and immersed in fibronectin for 4 hours. In parallel to this, autologous cells (endothelial cells) were taken from a recipient's living body to be transplanted to prepare a cell-containing solution. The cell-containing solution used herein was prepared by culturing the autologous cells thus taken in a culture plate containing M199 for 5 days, removing the autologous cells cultured from the culture plate with trypsin, and adding to M199. The cells were cultured in M199 supplemented with FBS (Fetal Bovine Serum IWK-500, manufactured by Iwaki), antibiotics (penicillin/streptomycin mixed solution) and FGF-2 (manufactured by Pepro Tech Ec Ltd.).

Thereafter, the blood-vessel tissue was immersed in the cell-containing solution for about 4 hours while rotating the blood-vessel tissue up and down. After the cell-seeding process, the blood-vessel tissue was observed under a microscope and a magnified view of the blood-vessel tissue was taken by a camera. The state of the autologous cells (endothelial cells) seeded in the blood-vessel tissue was observed.

Figure 12:
FIG. 12 is a magnified photomicrograph of the living organism tissue obtained in Example 3.

As a result, it was found that the autologous cells were seeded in virtually the entire blood-vessel tissue, as shown in FIG. 12. Actually, about 8.50 autologous cells in average were attached per unit area (1 mm$^2$) of the blood-vessel tissue. The ratio (density) of the area occupied by autologous cells per unit area (1 mm$^2$) of the blood-vessel tissue was about 18% in average.

Example 4

In Example 4, after the blood-vessel tissue was treated in the same steps as in Example 3, the cell-containing solution was circulated in the circulation apparatus 10A under the same flow conditions as in Example 1.

To explain more specifically, after the blood-vessel tissue was immersed in the cell-containing solution maintained to stand still for about 48 hours, it was rotated up and down for about 4 hours. Then, the cell-containing solution was allowed to flow so as to correspond to the blood flow in the human aorta. The blood-vessel tissue was left alone in the flow for one hour. Thereafter, the state of the autologous cells seeded in the blood-vessel tissue was observed in the same manner as in Example 3.

Figure 13:
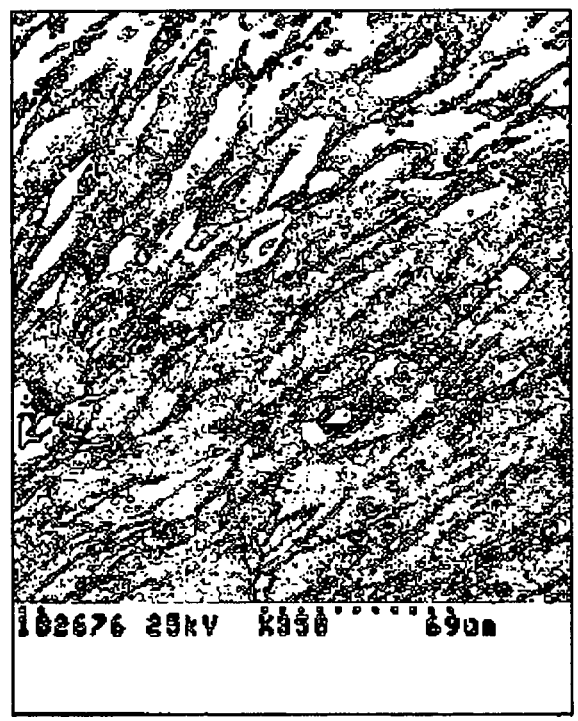
FIG. 13 is a magnified photomicrograph of the living organism tissue obtained in Example 4.

As a result, it was observed that the autologous cells were seeded uniformly in virtually the entire area of the blood-vessel tissue and that the autologous cells are aligned in the direction of the flow of the cell-containing solution, as shown in FIG. 13. In addition, compared to Example 3, the density of cells increased since the autologous cells proliferated. In this Example, the number of autologous cells attached to the blood-vessel tissue per unit area (1 mm$^2$) was about 2170 in average. The ratio (density) of the area occupied by the autologous cells per unit area (1 mm$^2$) of the blood-vessel tissue was about 63% in average.

Example 5

Example 5 was performed in the same manner as in Example 4 except that a step of maintaining the blood-vessel tissue to stand still in the cell-containing solution and a step of rotating the blood-vessel tissue up and down, were performed in reverse order. To explain more specifically, in this Example, the blood-vessel tissue immersed in the cell-containing solution was rotated up and down for about 4 hours and then, the blood-vessel tissue was immersed in the cell-containing solution in a standstill state for 48 hours. Then, the cell-containing solution was allowed to flow so as to correspond to the human blood flow in the aorta and the blood-vessel tissue was left alone in the flow for one hour. The other conditions were the same as in Example 4. Thereafter, the state of the autologous cells seeded in the blood-vessel tissue was observed in the same manner as in Example 4.

As a result, the autologous cells are proliferated and increased in density in the same as in Example 4. Other than this, the autologous cells are seeded more uniformly in the entire area than in Example 4.

Example 6

Example 6 was performed in the same manner as in Example 5 except that the time for leaving a blood-vessel tissue in the flow of the cell-containing solution prepared in the same conditions as in Example 5 was set at 48 hours.

As a result, the seeded cells proliferated and covered over virtually the entire surface of the blood-vessel tissue.

Example 7

Example 7 was performed in the same manner as in Example 6 except that the flow conditions of the cell-containing solution were changed. To explain more specifically, the average flow rate of the cell-containing solution was set at 2 L per minute and the average liquid pressure of the cell-containing solution was set at about 20 mmHg.

As a result, virtually the same effect as in Example 6 was obtained. In other words, if the cell-seeding method of the present invention was applied, even if the flow conditions of a cell-containing solution are changed in view of the state of blood flow and the heart-valve position of a recipient (a patient to be transplanted), the autologous cells seeded in the blood-vessel tissue proliferate and cover almost the entire surface thereof. Thus, generally, bioprosthetic valves can be prepared to meet the conditions for heart valves from those of adults to those of children who differ in amount of blood circulating in body, and those who differ in blood pressure.

Comparative Example 2

An experiment was performed as Comparative Example to Examples 3 to 7. The blood-vessel tissue was left alone without rotating up and down, in order to make comparison with Example 3, and the state of autologous cells seeded in the blood-vessel tissue was observed in the same manner as in Example 3.

As a result, the autologous cells were seeded but non-uniformly in the blood-vessel tissue. Accordingly, the number of autologous cells seeded in the blood-vessel tissue was significantly reduced compared to Examples 3 to 7.

From the results in the foregoing, the number of autologous cells attached to the tissue in Examples 3 to 7 is significantly larger than in Comparative Example 2. That is, a high cell-seeding effect was obtained. In particular, when the blood-vessel tissue is immersed in a pulsatile flow of a cell-containing solution, the orientation of cells is improved. In addition, the cells are activated and the function of cells is improved, with the result that a larger number of cells can be seeded.

The present invention is applicable to a cell-removing process for other living organism tissues which blood is in contact with other than the blood-vessel tissue containing the aortic valve as explained in the embodiment. Furthermore, the present invention is applicable to a process for an allogeneic bioprosthetic valve other than a xenogenic bioprosthetic valve.

In the cell-removing method according to the present invention, the living organism tissue processing apparatus 10 explained in the embodiment is not essentially used. Various apparatuses and means may be used as long as they can remove cells. In other words, any apparatuses can be used as long as it can provide a predetermined pulsatile flow of a solution for use in immersing a living organism tissue during the cell-removing process and/or it can apply microwave to the living organism tissue.

As explained in the foregoing, according to the present invention, original cells present in a living organism tissue such as a xenogenic bioprosthetic valve can be removed and the biocompatibility of the living organism tissue after transplant can be enhanced.

INDUSTRIAL APPLICABILITY

The present invention can be used in processing a bioprosthetic valve taken from an animal including a human to a state capable of being transplanted in a human body.

The invention claimed is:

1. A cell-removing method for removing original cells from a living organism tissue after the living organism tissue is removed from a transplant donor and before the living organism tissue is implanted into a transplant recipient, comprising:

immersing the living organism tissue in a cell-removing solution, the cell-removing solution flowing in a state of a pulsatile flow, while irradiating the living organism tissue with microwave.

2. The cell-removing method according to claim 1, wherein the microwave is applied while rotating the living organism tissue relative to a microwave irradiation site.

* * * * *